United States Patent [19]
Nishikawa

[11] Patent Number: 4,658,669
[45] Date of Patent: Apr. 21, 1987

[54] VERTICAL MOVEMENT AND FIXTURE DEVICE

[75] Inventor: Kazuo Nishikawa, Uji, Japan

[73] Assignee: Kabushiki Kaisha Morita Seisakusho, Kyoto, Japan

[21] Appl. No.: 879,381

[22] Filed: Jun. 27, 1986

[30] Foreign Application Priority Data

Jul. 1, 1985 [JP] Japan .................. 60-100992[U]

[51] Int. Cl.⁴ ............................................. G05G 5/06
[52] U.S. Cl. .................................... 74/531; 74/106
[58] Field of Search .............. 74/531, 106, 520; 188/67, 40

[56] References Cited

U.S. PATENT DOCUMENTS

| | | | |
|---|---|---|---|
| 2,064,899 | 12/1936 | Finer et al. | 188/67 UX |
| 3,807,253 | 4/1974 | Belzile | 74/520 X |
| 4,429,771 | 2/1984 | Martin | 74/106 X |

FOREIGN PATENT DOCUMENTS

2549102  5/1977  Fed. Rep. of Germany ........ 188/67

*Primary Examiner*—Andrew V. Kundrat
*Attorney, Agent, or Firm*—Koda and Androlia

[57] ABSTRACT

A vertical movement and fixture device to be used for, for instance, a dental tomograph for photographing entire jaw including a vertical support having a vertical groove inside, a block base which is slidably fit in the groove and is fixed to a slider and a means for fixing and releasing the block base at any desired position in the groove, the means for fixing and releasing the base block comprising a horizontal shaft, a pair of links each one end of which is swingably connected to one end of the horizontal shaft respectively, a pair of brake shoes which are respectively secured to the other ends of the links, and an operation member which supports and vertically moves the other end of the horizontal shaft. According to the device, the block base can be firmly fixed to and released from the support simply by applying slight control force and the cost of the device is low since its construction is entirely mechanical. Therefore, the device of the present invention is far more advantageous than conventional devices.

4 Claims, 5 Drawing Figures

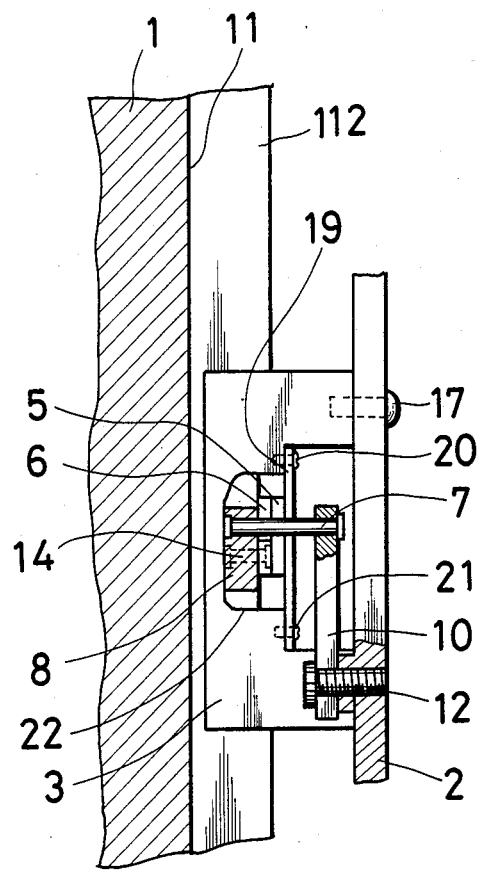
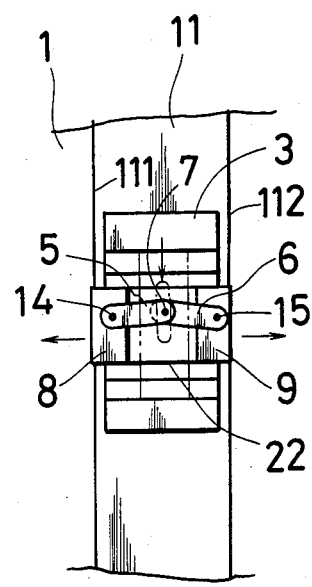
FIG. 2
FIG. 3

VERTICAL MOVEMENT AND FIXTURE DEVICE

BACKGROUND OF THE INVENTION

1. Field of the Invention

The present invention relates to a device for vertically moving a slider along a vertical support, fixing the slider at any desired position and releasing the slider from the support, more particularly, concerns with an improvement in a vertical movement and fixture device comprising a groove disposed inside the support, a block base slidably fit in the groove, a slider fixed to the block base and a means for fixing and releasing the block base at any desired position.

2. Prior Art

In the case of the dental tomograph P for photographing entire jaw shown in FIG. 5, for example, it is essential to vertically move and fix a slider 2 comprising the above-mentioned groove, block base, slider and means for fixing and releasing the block base at any desired position on a vertical support 1. In this case, the slider 2 includes an X-ray photographing arm A comprising an X-ray generator X and an X-ray film F secured to both ends of the arm, a carriage C for hanging the arm, a patient's head holding member H, other mechanical elements, electrical circuits and the like. Therefore, a block base 3 (not shown in FIG. 5) must be firmly fixed to the walls of the groove 11 of the support 1. In addition, since the slider needs to be released frequently during use, the release operation must be easy.

A conventional means for fixing and releasing the slider uses an electromagnetic brake between the slider and the support. This type can deliver great fixing force and promptly release the force. However, since this type needs electrical circuits, the cost is high. This is a great disadvantage. A screw tightening method is also used to fix the slider on the support. In the case of this entirely mechanical type, the slider cannot be fixed or released by simple operation. Furthermore, it is difficult to obtain constant and great fixing force, since the fixing force of this type is dependent on the tightening force of the screw.

SUMMARY OF THE INVENTION

It is, therefore, an object of the present invention to eliminate these disadvantages, more particularly to provide an inexpensive device which can apply and release great fixing force between the block base and the groove of the support by simple operation.

BRIEF DESCRIPTION OF THE DRAWINGS

The embodiments of the present invention will be apparent from the following description and the accompanying drawings.

FIG. 2 is a vertical sectional side view of the assembly of the first embodiment;

FIG. 3 is a plan view illustrating the slider fixed to a support by brake shoes of the first embodiment;

DETAILED DESCRIPTION OF THE INVENTION

Figure 1:
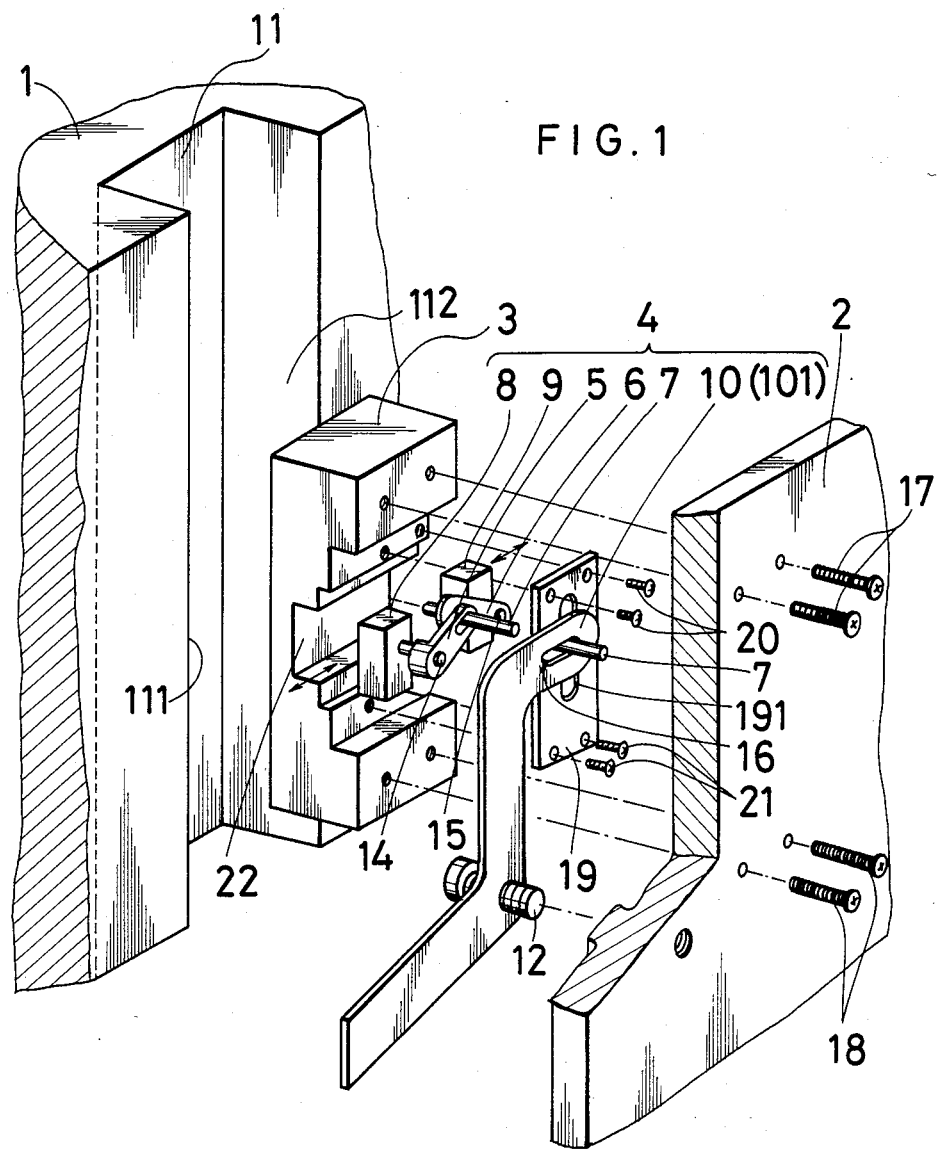
FIG. 1 is an exploded perspective view of the main section of the first embodiment of the present invention.

The device common to the first and second embodiments of the present invention includes a vertical support 1 having a vertical groove 11 inside, a block base 3 which is slidably fit in the groove 11 and is fixed to a slider 2, and a means 4 for fixing and releasing the block base 3 at any desired position in the groove 11. The means 4 for fixing and releasing the base block 3 comprises a horizontal shaft 7, a pair of links 5 and 6 each one of which is swingably connected to one end of the horizontal shaft 7, respectively, a pair of brake shoes 8 and 9 which are respectively mounted at the other (upper) ends of the links 8 and 9, and an operation member 10 which supports and vertically moves the other end of the horizontal shaft 7. In this construction, when the operation member 10 is lowered, the links 5 and 6 swing around the horizontal shaft 7 until the angle between the two links is almost 180 degrees. As a result, the brake shoes 8 and 9 are firmly pressed against the side walls 111 and 112 of the groove 11. FIGS. 1, 2 and 3 show the first embodiment of the present invention. In this embodiment, the brake shoes 8 and 9 are respectively mounted at the other (lower) ends of the links 5 and 6 via pivot shafts 14 and 15. The operation member 10 is a crank member 101 and one end of the horizontal shaft 7 is loosely inserted into the slot 16 disposed at the top of the crank member 101 and is supported by the crank member 101. The slider 2 (practically a box plate mounted on the front of the slider) is mounted on the front side of the block base 3 with screws 17 and 18. The crank member 101 is rotatably supported by a pivot shaft 12 which is installed on the slider 2. A mounting plate 19 having a slot 191 which allows the vertical movement of the horizontal shaft 7 is fixed to the block base 3 with screws 20 and 21. The links 5 and 6 are assembled and inserted in the recessed section 22 of the block base 3 so that the links can freely swing around the horizontal shaft 7 (see FIG. 2). In this first embodiment, the brake shoes 8 and 9 are firmly pressed against the side walls 111 and 112 as shown in FIG. 3 when the operation member 10, i.e., the crank member 101 is lowered. FIG. 3 clearly shows the operation of the brake shoes 8 and 9. With this embodiment which uses the crank member 101, a great braking effect is obtained by applying slight operation force to the crank member 101 due to a force magnification mechanism.

Figure 4:
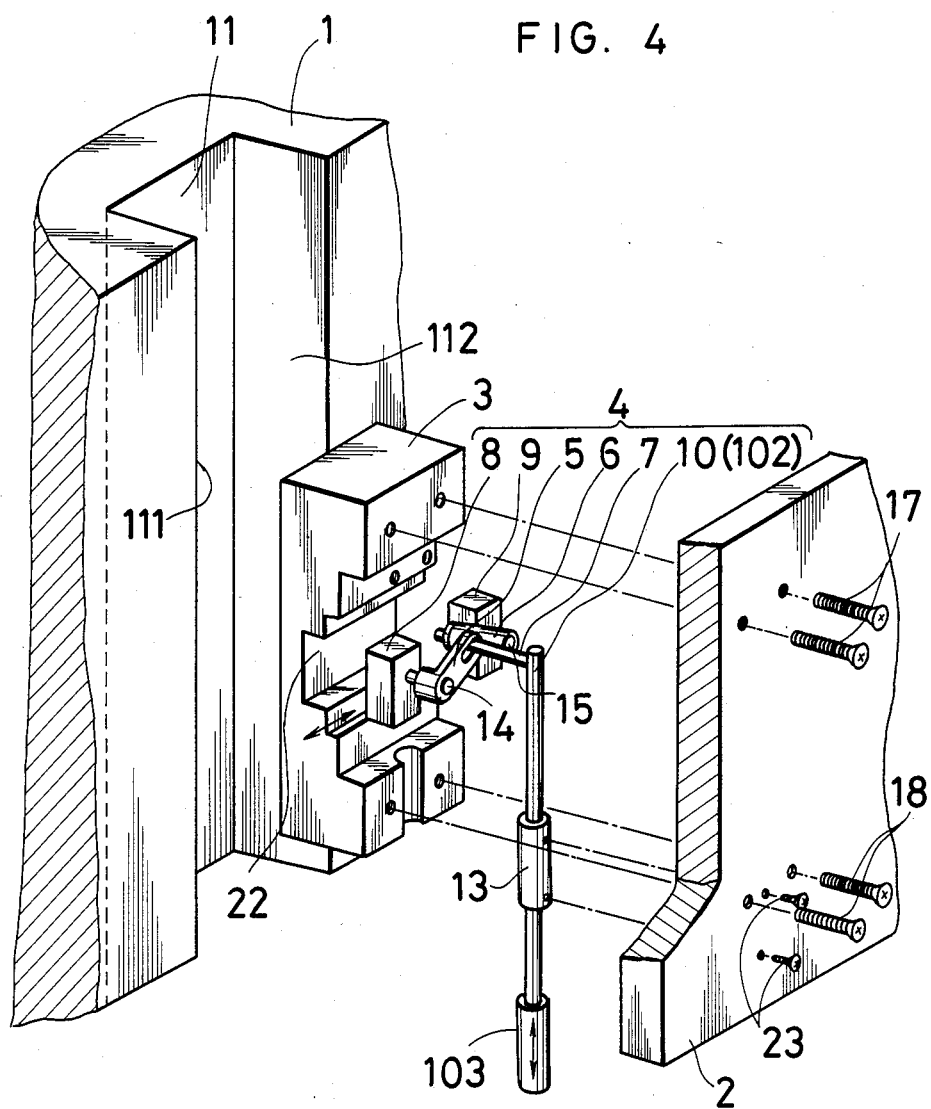
FIG. 4 is an exploded perspective view of the main section of the second embodiment.
Figure 5:
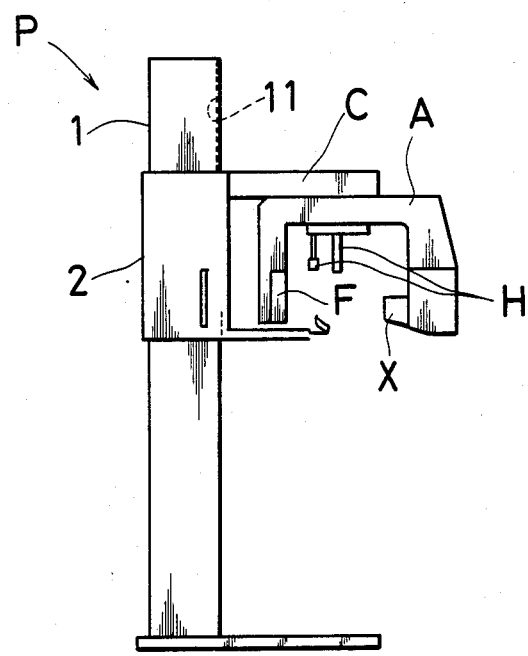
FIG. 5 is a side view of a dental tomograph for photographing entire jaw.

The second embodiment shown in FIG. 4 uses a rod member 102 as the operation member 10. As shown in FIG. 4, a sleeve 13 is fixed to the slider 2 with screws 23. The rod member 102 is inserted in the sleeve 13 so that the rod member 102 can vertically slide along the sleeve 13. The top end of the rod member 102 is fixed to the horizontal shaft 7. At the bottom end of the rod member 102, a control handle 103 is disposed.

Since the second embodiment is the same as the first embodiment in construction except the above-mentioned construction, the same construction is not explained any more. The mounting plate 19 is not shown in FIG. 4. By vertically sliding the rod member 102 of the second embodiment, the horizontal shaft 7 is moved up and down. When the horizontal shaft 7 is moved down, the angle between the links 5 and 6, which form a force magnification mechanism, increases to almost 180 degrees to firmly press the brake shoes 8 and 9 against the side walls 111 and 112. When the horizontal shaft 7 is moved up by the rod member 102, the braking effect is abruptly lost and the block base 3 is released from the side walls 111 and 112.

In this construction, when the operation member 10 lowered, the links 5 and 6 swing around the horizontal shaft 7 and the angle between the links increases to almost 180 degrees. Since the links 5 and 6 form a force magnification mechanism as described above, the brake shoes 8 and 9 which are respectively secured to the lower ends of the links 5 and 6 are firmly pressed against the two side walls 111 and 112 (facing each other) of the groove 11 to obtain great fixing force between the block base 3 and the support 1. In case the brake shoes 8 and 9 are connected to the links 5 and 6 via the pivot shafts 14 and 15, the pressure of the brake shoes is vertically applied to the side walls 111 and 112, thus the maximum braking effect is obtained.

When the horizontal shaft 7 is raised by the operation member 10, the pressure is abruptly lost and the base block 3 can be quickly released from the side walls 111 and 112. In the embodiments of the present invention, a force magnification mechanism is formed by the links 5 and 6 (including the brake shoes 8 and 9), the horizontal shaft 7, the recessed section 22 (described below) of the slide base 3 and the mounting plate 19, and the mechanism is controlled by the operation member 10.

As clearly understood by referring to the above description, the device of the present invention uses the links 5 and 6 and the horizontal shaft 7 to form a toggle link mechanism for the force magnification mechanism so that the brake shoes installed at the lower ends of the links 5 and 6 are firmly pressed against and released from the side walls 111 and 112 of the groove 11 disposed in the support 1 by controlling the operation member 10. Therefore, the block base 3 can be firmly fixed to and released from the support 1 simply by applying slight control force. Furthermore, the cost of the device is low, since its construction is entirely mechanical.

Accordingly, this device can completely eliminate the disadvantages of the conventional devices and is very useful when the device is used for an apparatus wherein a heavy slider is vertically moved and stopped at any desired position, such as a dental tomograph for photographing entire jaw.

Having described my invention as related to the embodiments shown in the accompanying drawings, it is my intention that the invention be not limited by any of the details of description, unless otherwise specified, but rather be construed broadly within its spirit and scope as set out in the accompanying claims.

I claim:

1. A vertical movement and fixture device including a vertical support having a vertical groove inside, a block base which is slidably fit in said groove and is fixed to a slider and a means for fixing and releasing said block base at any desired position in said groove, said means for fixing and releasing said base block comprising a horizontal shaft, a pair of links each one end of which is swingably connected to one end of said horizontal shaft respectively, a pair of brake shoes which are respectively secured to the other ends of said links via a pair of pivot shafts, and an operation member which supports and vertically moves the other end of said horizontal shaft so that when said operation member is lowered, said links swing around said horizontal shaft until the angle between said two links is almost 180 degrees whereby said brake shoes are firmly pressed against the side walls of said groove.

2. A vertical movement and fixture device according to claim 1, wherein said operation member comprises a crank member rotatably supported by a pivot shaft fixed to said slider and connected to said horizontal shaft at the top end.

3. A vertical movement and fixture device according to claim 1, wherein said operation member comprises a rod member which vertically slides in a sleeve fixed to said slider and is fixed to said horizontal shaft at the top end.

4. A vertical movement and fixture device according to claim 1, claim 2 or claim 3, wherein said brake shoes are connected to the lower ends of said links via pivot shafts.

* * * * *